(12) United States Patent
Smith

(10) Patent No.: US 8,518,362 B2
(45) Date of Patent: Aug. 27, 2013

(54) STABILIZATION AND IONIC TRIGGERING OF NITRIC OXIDE RELEASE

(75) Inventor: Daniel J. Smith, Stow, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 13/234,495

(22) Filed: Sep. 16, 2011

(65) Prior Publication Data

US 2012/0114547 A1    May 10, 2012

Related U.S. Application Data

(63) Continuation of application No. 10/565,573, filed as application No. PCT/US2004/023867 on Jul. 26, 2004, now abandoned.

(60) Provisional application No. 60/490,218, filed on Jul. 25, 2003.

(51) Int. Cl.
*C01B 21/24* (2006.01)

(52) U.S. Cl.
USPC ........................................................ 423/405

(58) Field of Classification Search
USPC ........... 423/385, 400, 405; 424/78.27, 78.35, 424/718
See application file for complete search history.

(56) References Cited

U.S. PATENT DOCUMENTS

| 5,519,020 | A  | * | 5/1996  | Smith et al. | 424/718 |
| 5,691,423 | A  | * | 11/1997 | Smith et al. | 525/377 |
| 6,451,337 | B1 | * | 9/2002  | Smith et al. | 424/445 |
| 6,511,991 | B2 | * | 1/2003  | Hrabie et al. | 514/315 |
| 2001/0041184 | A1 | * | 11/2001 | Fitzhugh et al. | 424/400 |
| 2002/0115559 | A1 | * | 8/2002  | Batchelor et al. | 502/159 |
| 2002/0136750 | A1 | * | 9/2002  | Benjamin et al. | 424/408 |
| 2003/0064028 | A1 | * | 4/2003  | Fine et al. | 424/43 |
| 2005/0036949 | A1 | * | 2/2005  | Tucker et al. | 424/45 |

FOREIGN PATENT DOCUMENTS

WO    WO 96/15797 A1 *  5/1996
WO    WO 98/13358 A1 *  4/1998

OTHER PUBLICATIONS

Smith et al. (XP-002157493), "Nitric Oxide-Releasing Polymers Containing the [N(O)NO]-Group," 1996, J. Med. Chem., 39, pp. 1148-1156.*
Benon H. J. Bielski, "Chemistry of Ascorbic Acid Radicals," Jun. 1, 1982, Ascorbic Acid: Chemistry, Metabolism, and Uses, Chapter 4, pp. 81-100.*

* cited by examiner

*Primary Examiner* — Melvin C Mayes
*Assistant Examiner* — Stefanie Cohen
(74) *Attorney, Agent, or Firm* — Renner Kenner Greive Bobak Taylor & Weber

(57) ABSTRACT

Provided is a method for producing nitric oxide that employs an ion exchange resin. Also provided is a method for producing nitric oxide that combines a salt with a gel or cream. A method is provided for producing nitric oxide that combines a pH adjuster with a diazeniumdiolate-containing compound or composition.

8 Claims, 8 Drawing Sheets

| NONOate-DOWEX | Half lives (hr) | |
|---|---|---|
|  | 32° C | 37° C |
| DETAN-DOWEX | 109 ± 9 | 51 ± 11 |
| EPN-DOWEX | 3.07 ± 0.68 | 2.33 ± 0.97 |
| MePN-DOWEX | 1.30 ± 0.31 | 0.68 ± 0.01 |
| PuN-DOWEX | - | - |

PBS pH 7.4

- Not determine yet.

| Putreanine based diazeniumdiolates | λ max (nm) | ϵ (mM⁻¹ cm⁻¹) | t ½ ᵃ (hr) 32° C | t ½ ᵃ (hr) 37° C |
|---|---|---|---|---|
| DETANO | 250 | 7.64[b] | 38.5 | 20.0[b] |
| EPN-Na | 250 | 6.2 | 1.41 ± 0.27 | 0.85 ±0.03 |
| MePN-Na | 245 | 4.5 | 2.08 ± 0.22 | 1.65 ± 0.001 |
| PuN-Na | 240 | 3.4 | 0.65 ± 0.24 | 0.52 ±0.16 |

[a] PBS pH 7.4
[b] Hrabie, J.A., Klose, J.R., Wink, D.A., et al. New nitric oxide-releasing zwitterions derived from polyamines. J. Org. Chem. 58, 1472-1476 (1993).

Figure 7

| NONOate-DOWEX | Half lives (hr) | |
| --- | --- | --- |
| | 32° C | 37° C |
| DETAN-DOWEX | 109 ± 9 | 51 ± 11 |
| EPN-DOWEX | 3.07 ± 0.68 | 2.33 ± 0.97 |
| MePN-DOWEX | 1.30 ± 0.31 | 0.68 ± 0.01 |
| PuN-DOWEX | - | - |

PBS pH 7.4
- Not determine yet.

Figure 8

STABILIZATION AND IONIC TRIGGERING OF NITRIC OXIDE RELEASE

CROSS-REFERENCE TO RELATED APPLICATIONS

This application is a continuation of U.S. patent application Ser. No. 10/565,573, filed Feb. 26, 2007, which was a National Stage filing of International Application No. PCT/US04/23867, filed Jul. 26, 2004, which claims priority to U.S. Provisional Patent Application Ser. No. 60/490,218, filed Jul. 25, 2003, all of which are herein incorporated by reference in their entirety.

FIELD OF THE INVENTION

This invention relates to a method for producing nitric oxide. More specifically, this invention relates to using ionic exchange resins in the production of nitric oxide. This invention is also directed to using pH adjusters in combination with diazeniumdiolate-containing compounds (NONOates) to produce nitric oxide. The invention is further directed to producing nitric oxide by mixing a cream with a salt.

BACKGROUND OF THE INVENTION

Ionic Exchange Resins

Ionic exchange resins are known. Most modern ionic exchange resins, or ionic exchangers, consist of a synthetic polymer backbone or matrix to which is attached a functional group that gives each ionic exchanger its specific properties. Ionic exchange resins are produced in various physical forms depending on the end use for the resin. Most commonly, they are used as small spherical beads or granules, but they can be made into membranes, fibers, tubes, cloth, or foams. By special manufacturing techniques, the polymers, especially in the bead form, may be made with porous structures instead of the conventional solid gel resin structure. Such resins are called macroporous or macroreticular resins.

The functional groups that are distributed throughout the resin structure contain fixed electric charges or ion-active groups, each of which is associated with a mobile counter ion of opposite charge. These mobile ions are capable of reacting with or exchanging with other ions of like sign when they are in contact with a solution containing such ions. It is important that ionic exchange resins swell to a certain extent in aqueous or liquid solution so that the solution can diffuse into the resin and come into contact with the active sites.

When the fixed electrical charges within the resin matrix are negative (when the fixed functional group is a sulfonic group, for example), the mobile ions are cations and the resin is said to be a cationic exchange resin. Conversely when the fixed groups are positively charged, the mobile ions are anions and the resin is an anionic exchanger.

The polymer matrices are usually cross-linked to make them insoluble and to give them mechanical strength and stability. The extent of cross-linking must be controlled so as to give good mechanical properties to the resin while permitting enough water absorption and swelling to ensure good ionic exchange activity.

Ionic exchange has been defined as the reversible interchange of ions between a solid and a liquid phase in which there is no permanent change in the structure of the solid. This means that ionic exchangers are not consumed by ordinary usage, but when they are exhausted, they can be regenerated or reconverted to their original state and reused. Ionic exchange is regarded as a unit process in chemical engineering and it has many applications. One of the best known and largest applications is water softening, in which calcium and magnesium ions, which cause water hardness, are removed from the water and exchanged for sodium ions from the resin. When the resin is exhausted, it is brought back to its original state by treatment with a sodium chloride solution. By a more complex process, water may be not only softened, but completely deionized. Ionic exchange resins are widely used to treat boiler feed water, process water, and to perform a large number of separations and reactions in the manufacture of chemicals, foods, pharmaceuticals, electronic devices, and many other products.

Ionic exchange is a widespread phenomenon in nature, occurring in living cells and in soils, for example. Ionic exchange materials include silicates, phosphates, fluorides, humus, wool, proteins, cellulose, alumina, glass, and many others. The first industrial ionic exchangers were probably inorganic aluminum silicates, used for softening water and treating sugar solutions. Later on, it was discovered that sulfonated coal is a relatively effective ionic exchange material, but such materials are fragile and are useful only under restricted operating conditions. In the United States nearly all ionic exchange applications use synthetic polymer resins.

Nitric Oxide

At room temperature nitric oxide (NO) is a gas that can participate in many chemical reactions. There are many known biological and medical uses of NO. A nonlimiting list of some of these uses include:

Blood Flow: NO relaxes the smooth muscle in the walls of the arterioles. At the time of each systole, the endothelial cells that line the blood vessels release a puff of NO. This diffuses into the underlying smooth muscle cells causing them to relax and thus permit a surge of blood to pass through easily.

Nitroglycerine, which is often prescribed to reduce the pain of angina, does so by generating nitric oxide, which relaxes the walls of the coronary arteries and arterioles.

NO also inhibits the aggregation of platelets and thus keeps inappropriate clotting from interfering with blood flow.

Kidney Function: Release of NO around the glomeruli of the kidneys increases blood flow through them thus increasing the rate of filtration and urine formation.

Penile Erection: The erection of the penis during sexual excitation is mediated by NO released from nerve endings close to the blood vessels of the penis. Relaxation of these vessels causes blood to pool in the blood sinuses producing an erection.

The popular prescription drug sildenafil citrate inhibits the breakdown of NO and thus enhances its effect.

Peristalsis: The wavelike motions of the gastrointestinal tract are aided by the relaxing effect of NO on the smooth muscle in its walls.

Because of the many well-known uses of NO, there is therefore a need in the art for additional methods directed to NO production and its delivery at target locations.

SUMMARY OF THE INVENTION

In general the present invention provides a method for producing nitric oxide comprising producing nitric oxide by using an ionic exchange resin.

The present invention also includes a method for producing nitric oxide comprising mixing a salt with a cream, gel, or combination thereof to produce nitric oxide.

The present invention also includes a method for producing nitric oxide comprising producing nitric oxide by adding a pH adjuster to a nanofiber having a diazeniumdiolate functional group.

The present invention further includes a method for producing nitric oxide comprising producing nitric oxide by adding a pH adjuster to a nanoparticle having a diazeniumdiolate functional group.

The present invention includes an embodiment that uses an ion exchange resin, and that embodiment allows for ionic triggering of the release or production of nitric oxide. An additional advantage of the present invention is that it provides a gel or cream delivery system for producing or delivering nitric oxide to a target region or specific location. An additional advantage to using a cream or gel delivery system is that the surface area of the delivery vehicle provides an advantage over other prior art methods for delivering nitric oxide.

Terminology

Nitric oxide is a well-known compound that is a colorless gas at room temperature.

Ionic exchange resins are well-known. An ionic exchange resin is typically a polymer with electrically-charged sites at which one anion may replace another. Synthetic ionic exchange resins are usually cast as porous beads with a considerable external and porous surface area where ions can attach. Anionic exchange resins and cationic exchange resins are two specific types of ionic exchange resins. Anionic exchange resins are exchange resins that have a plurality of positively-charged sites, and cationic exchange resins are ionic exchange resins that have a plurality of negatively-charged sites.

Counter ions are the ions that form ion pairs with the charged sites on an ionic exchange resin. More specifically, when an ionic exchange resin is a cationic exchange resin, the counter ion is a cation that forms an ion pair with a negatively-charged site on the exchange resin. When the ionic exchange resin is an anionic exchange resin, the counter ion is an anion that forms an ion pair with the positively-charged site on the anionic exchange resin.

A salt is generally known as a compound that is formed when the hydrogen atom of an acid is replaced by a metal or a metal equivalent.

A pH adjuster is a composition that either increases or decreases the of a reaction medium.

A nanofiber is a fiber having a characteristic dimension on the nanoscale.

A nanoparticle is a particle having a characteristic dimension on the nanoscale.

BRIEF DESCRIPTION OF THE DRAWINGS

FIG. 7 is a table of the summary of physical properties of putreanine based diazeniumdiolates.

FIG. 8 is a table of kinetics results of NONOates with an ion exchange resin (NONOate-IER).

DETAILED DESCRIPTION OF ILLUSTRATIVE EMBODIMENTS

Figure 1:
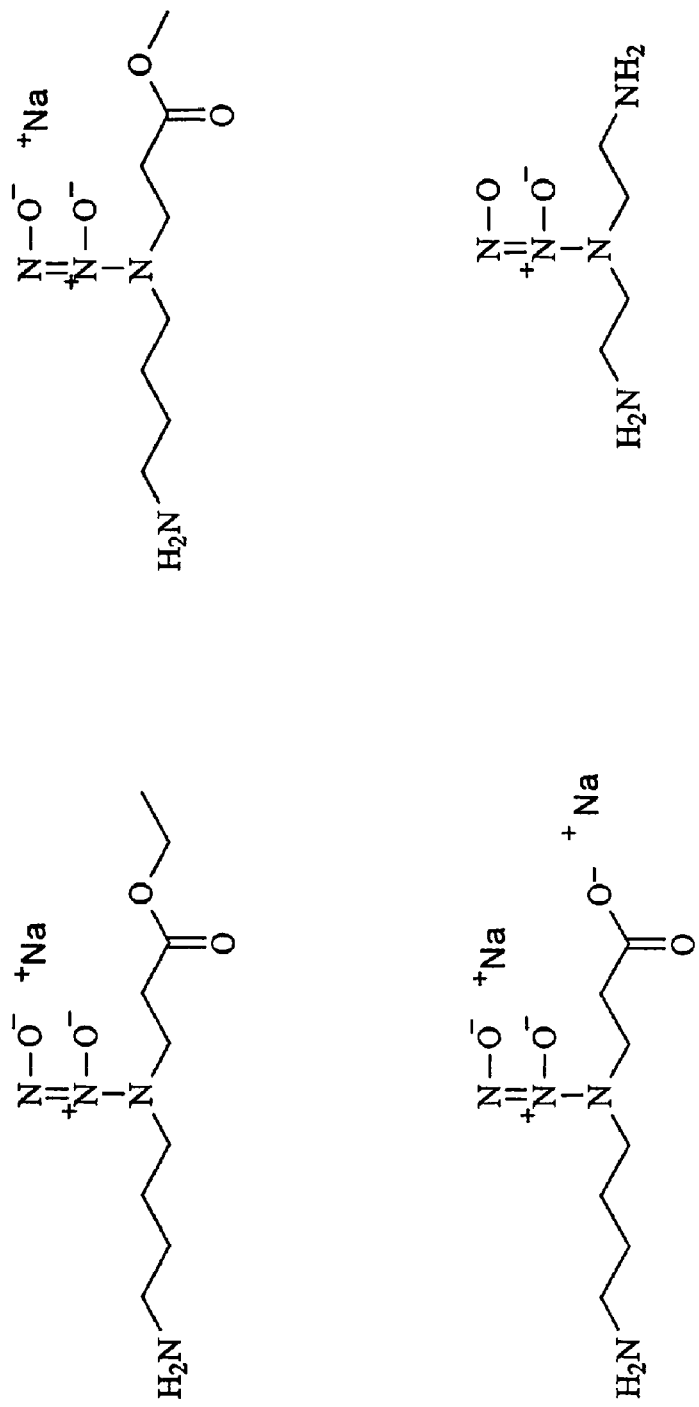
FIG. 1 provides structures of polyamine NONOates. Specifically provided are ethyl putreanate diazeniumdiolate sodium salt (EPN—Na), methyl putreanate diazeniumdiolate sodium salt (MePN—Na), putreanine diazeniumdiolate sodium salt (PuN—Na), and diethylenetriamine diazeniumdiolate (DETA-NO)
Figure 2:
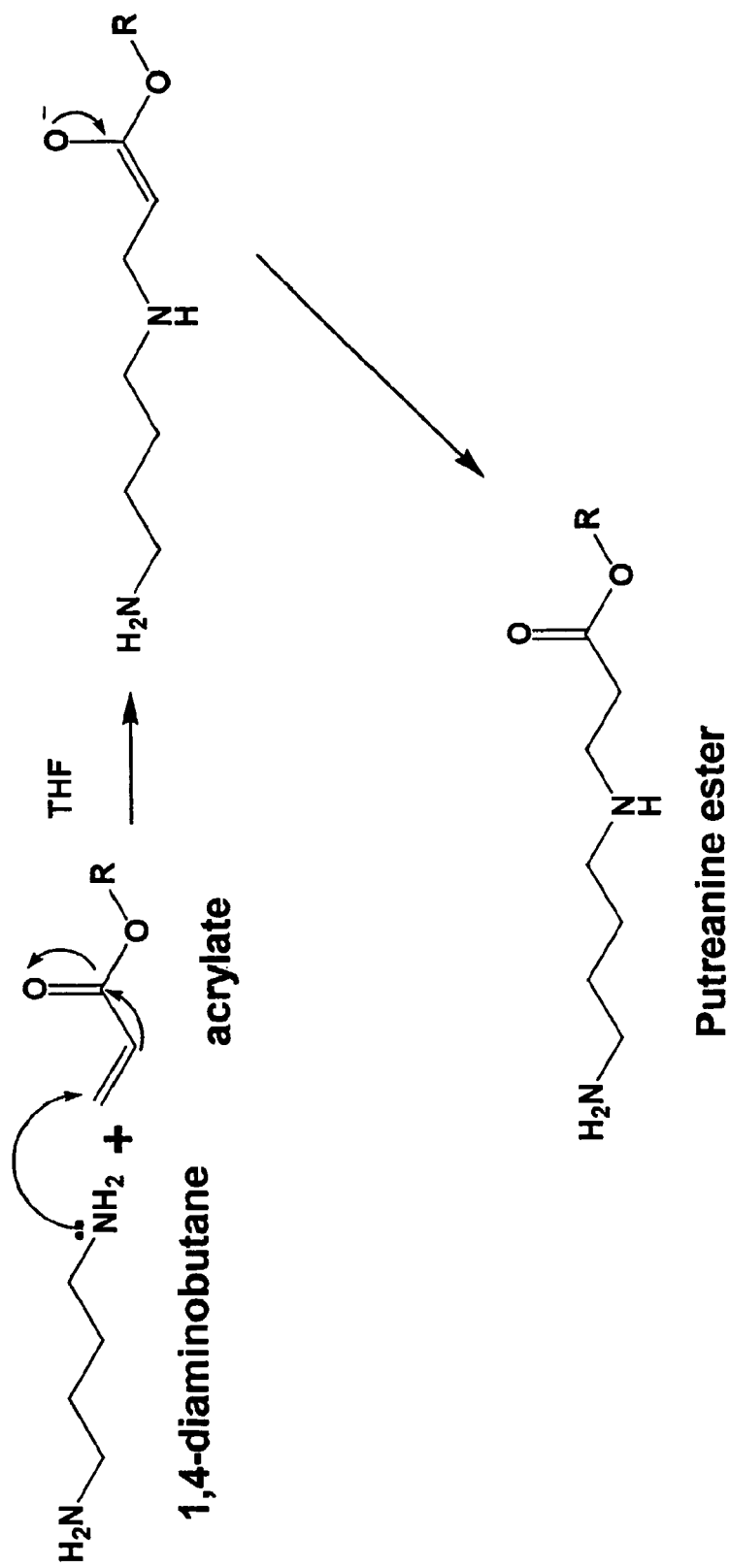
FIG. 2 is general synthesis of putreanine esters.

This invention is generally directed to a method for producing nitric oxide by using an ion exchange resin. The ionic exchange resin is either a cationic exchange resin or an anionic exchange resin. Using an ionic exchange resin allows a user to ionically trigger the release of anionic or cationic reactants from an ion exchange resin, whereby the anionic or cationic reactants preferably proceed to participate in producing nitric oxide via a chemical reaction.

This invention is further directed to producing NO by using a pH adjuster used in combination with a diazeniumdiolate-containing composition.

This invention is further directed to mixing a salt with a cream, gel, or combination thereof to produce nitric oxide.

As mentioned above, an embodiment of this invention preferably employs an ionic exchange resin that forms an ion pair with a counter ion, wherein the counter ion can be displaced by a different and typically stronger cation or anion. There is no limitation on useful ion exchange resins, and any ion exchange resin can be employed in the present invention. The cation or anion that displaces a counter ion on the ionic exchange resin can come from any source. Preferably, the displacing anion or cation is generated from a salt that has dissociated. Salts that are useful in generating these displacing cations and anions can be selected from the group consisting of sodium chloride, sodium phosphate, or sodium acetate. There is, however, no limitation on the salts that can be used in the present invention.

When an anionic exchange resin is employed, its counter ion is preferably selected from the group consisting of ascorbate, nitrate, a diazenium-diolate (a NONOate functional group) containing compound, or a combination thereof. There is, however, no limit on the anionic counter ions that can be used in this invention.

In an embodiment of the present invention, the ionic exchange resins are preferably positioned or reside in a cream, gel, or combination thereof. Employable creams and gels include ion-free hydrogels, off-white-oil-in-water vanishing cream, or combinations thereof. The cream or gel preferably provides an inert reaction medium wherein the ionic exchange resins can reside. The cream or gel also preferably provides a medium or phase wherein a salt can dissociate and thereby form a salt cation and a salt anion. A salt cation or salt anion can displace a counter ion and thereby facilitate nitric oxide production.

In a preferred embodiment, an ascorbate anion is a counter ion on an anionic exchange resin. The ascorbate anion preferably reacts with a hydrogen cation to produce ascorbic acid. Additionally, a nitrite counter ion preferably reacts with the ascorbic acid to produce nitric oxide.

In yet another embodiment, a diazeniumdiolate-containing compound is a counter ion on an anionic exchange resin that preferably reacts with a hydrogen cation to produce nitric oxide.

In still another embodiment, the diazeniumdiolate-containing compound is a polymer having a diazeniundiolate functional group. More preferably, the polymer is a polyethylenimine nanofiber having a diazeniumdioate functional group. More preferably, the nanofiber is an electrospun nanofiber, and any electrospun nanofiber having a diazeniumdiolate functional group can be employed. Preferably, a pH adjuster is added to a nanofiber having a diazeniumdioate functional group in order to produce nitric oxide. The pH adjuster is preferably selected from phosphate, lactate, citrate, or combinations thereof. There is no limitation on useful polymers or pH adjusters that can be employed.

In yet another embodiment, nitric oxide can be produced by adding a pH adjuster to a nanoparticle having a diazeniumdiolate functional group. Preferably, the nanoparticle is made of cellulose, polystyrene, cm cellulose, chitosan or a combination thereof. In this embodiment, the pH adjuster is selected from phosphate, lactate, citrate, or combination thereof. There is no limitation on useful polymers or pH adjusters that can be employed.

In still another embodiment, the nanoparticle having a diazeniumdiolate functional group is within or attached to a nanofiber. This can be achieved by incorporating the nanoparticle into an electrospinnable solution following by electrospinning.

In another embodiment, a nitrite anion forms an ion pair with an anionic exchange resin. For this particular embodiment, the ion pair will herein be referred as the exchange-resin composition. The exchange-resin composition is preferably in the presence of dry ascorbic acid, such that a dry mix of the exchange-resin composition and ascorbic acid is created. To this dry mix of the exchange-resin composition and ascorbic acid, a gel having a salt is added to the dry mix. The salt preferably dissociates or is dissociated within the gel. The dissociated salt forms a salt cation and a salt anion within the gel. The salt anion preferably displaces the nitrite counter ion and facilitates the nitrite counter ion to react with the ascorbic acid and thereby produces nitric oxide.

In another embodiment, a diazeniumdiolate-containing composition is a counter ion on an anionic exchange resin. Preferably, this exchange resin and its diazeniumdiolate-containing counter ion is suspended in a salt-free gel. The gel is then applied to a target region on skin or tissue, and salt from the skin or tissue preferably dissociates within the salt-free gel to thereby create salt anions and salt cations. The salt anions preferably proceed to exchange the counter ion, i.e., the diazeniumdiolate-containing compound, away from the exchange resin. Once the diazeniumdiolate compound is no longer a counter ion on the exchange resin, the diazeniumdiolate functional group preferably reacts to produce nitric oxide.

In yet another embodiment, an anionic exchange resin and a cationic exchange resin are employed in combination. Preferably, the anionic exchange resin has nitrite as a counter ion, and cationic exchange resin has protons as a counter ion. These two exchange-resin compositions, i.e., the anionic exchange resin in combination with its nitrite counter ion and the cationic exchange resin in combination with its proton or hydrogen counter ion are either in a dry mix or suspended within an ion-free gel. Upon addition of a salt to the gel, the salt dissociates and the salt cation displaces the hydrogen counter ion. Additionally, these salt ions displaces the nitrite counter ion. Once the anionic counter ion and the cationic counter ion are displaced from their respective exchange resins, the nitrite and hydrogen cation react to produce nitric oxide.

And still another embodiment, three anionic exchange resins are employed. A first ionic exchange resin is an anionic exchange resin wherein nitrite is the counter ion. The second ionic exchange resin is an anionic exchange resin wherein ascorbate in the counter ion. The third ionic exchange resin is a cationic exchange resin wherein hydrogen is the counter ion. Preferably, the first, second, and third ionic exchange resin compositions, i.e., each of these exchange resins in combinations with it's respective counter ion, are mixed within an ion-free gel. To the gel, a salt is added. The salt then dissociates and creates a salt cation and a salt anion. The salt cation preferably displaces the hydrogen counter ion on the third cationic exchange resin. Once displaced from its cationic exchange resin, a hydrogen cation reacts with an ascorbate counter ion to produce ascorbic acid. The ascorbic acid then proceeds to react with nitrite on the first anionic exchange resin to thereby yield nitric oxide.

Experimental

In order to demonstrate the practice of the present invention, the following examples have been prepared and tested. The examples should not, however, be viewed as limiting the scope of the invention. The claims will serve to define the invention.

Synthesis of Polyamines Derivatives: Putreanine Esters

Synthesis of Ethyl Putreanate (EP)

The synthesis was begun by dissolving 5 ml of ethyl acrylate (46.1 mmol) in 150 ml distilled THF which was dispensed into an addition funnel. This solution was added dropwise over 8 hours with constant stirring by a magnetic stirrer to a solution of three molar excess (14 ml, 138 mmol) of 1,4-diaminobutane in 200 ml of distilled THF. Once all of the ethyl acrylate was added, the reaction was stirred at room temperature for an additional 16 hours. The reaction was performed under nitrogen atmosphere. After this period of time the solvent (THF) was removed by roto-evaporation to leave an oily product (light yellow color). The 1,4-diaminobutane was removed by bulb-to-bulb vacuum distillation [17].

Hydrolysis of EP: Putreanine Sulfate Salt

This reaction was done by dissolving 3.18 g of EP in deionized water followed by The addition of 1 ml of concentrated sulfuric acid. The reaction mixture was allowed to reflux for one hour at 50-60° C. The solvent was removed by roto-evaporation leaving an oily clear product. Hot ethanol was added to the reaction flask. The crystals were formed after being kept in the refrigerator overnight [18]. They were filtered and washed with cold isopropyl alcohol and then dried under nitrogen atmosphere.

Nitric Oxide Modification

Sodium Salt of Methyl Putreanate NONOate (MeN—Na)

The NO modified compound was prepared by dissolving ethyl putreanate in 1.5 excess molar ratio of MeONa/MeOH, in a high pressure glass bottle (ACE Glass) with a magnetic stir bar. The stirred mixture was purged with nitrogen gas and then connected to a NO gas tank. The mixture was then brought to 100 psi of NO and left to react for 8 days under continuous stirring. After this time the NO gas was released, and the mixture was purged and flushed with nitrogen. The product was isolated by removal of solvent using a roto evaporator. The creamy color product (solid) was dried under the hood. The presence of the NONOate was confirmed by UV absorbance at 245 nm.

Sodium Salt of Putreanine NONOate (PuN—Na)

The NO modified compound was prepared by dissolving "putreanine sulfate salt" in 1.5 excess molar ratio of MeONa/MeOH in a high pressure glass bottle (ACE Glass) with a magnetic stir bar. The stirred mixture was purged with nitrogen gas and then connected to NO gas tank. The mixture was then brought to 100 psi of NO and left to react for 8 days under continuous stirring. After this time the NO gas was released, and the mixture was purged and flushed with nitrogen. The product was isolated by removal of solvent using a roto evaporator. The sample was then washed with ethyl ether. The white product (solid) was dried with air at room temperature. The presence of the NONOate was confirmed by UV absorbance at 240 nm.

Sodium Salt of Ethyl Putreanate NONOate (EPN—Na)

The NO modified compound was prepared by dissolving ethyl putreanate in 1.5 excess molar ratio of EtONa/EtOH in high pressure glass bottle (ACE Glass) with a magnetic stir bar. The stirred mixture was purged with nitrogen gas and then connected to a NO gas tank. The mixture was then brought to 100 psi of NO and left to react for 8 days under continuous stirring. After this time the NO gas was released, and the mixture was purged and flushed with nitrogen. The product was isolated by removal of solvent using a roto evaporator. The sample was washed then with ethyl ether leaving a yellow product (solid). The presence of the NONOate was confirmed by UV absorbance at 250 nm.

NO Donors Loading

Loading

A 1×4 400 ionic exchanger resin (IER), available as DOWEX, was treated with 1M solution of sodium hydroxide for 24 hours, in order to modify the chloride ions of the resin with hydroxyl groups. The sample of the treated resin was washed with deionized water until neutral and then dried. A flame test was used to confirm the removal of chloride ions; a positive result for the presence of chloride is an observable green color. NONOates were added to the resin in cold water, and the sample was kept on ice and stirred overnight. Then the sample was washed several times with deionized water and dried under nitrogen.

Stability Tests of NONOate-IER

A sample of NONOate-IER was analyzed using a UV spectrophotometer. A 1M solution of sodium chloride was used to exchange the NONOate from the resin. To determine the stability of the NONOate-IER, the sample was kept in water for a few days, taking the UV absorption in the region of 220-400 nm every 24 hours.

Nitric Oxide Release Kinetic Experiments

NO release profiles were performed by rapidly dissolving approximately 10.0 mg of the NONOate in 25 ml of PBS solution at physiological conditions (pH 7.4). The same stock solution of the buffer was used for baseline determination. The kinetic program was set up to keep a constant temperature of the sample (25° C. or 37° C.) and also to take measurements at the maximum absorptivity every 3 minutes for 20 hours. The rate of NO release (k) was determined with the best fit curve to the first order exponential decay [$\ln(abs_{inj}/abs)$ vs. time] using a spread sheet application, available as MICROSOFT OFFICE EXCEL 2002. The half-life of each NONOate was determined with the following equation:

$$t_{1/2} = -\ln(0.5)/k$$

The same procedure was followed for the nitric oxide release from NONOate-IER using 2.6 mg in 4 ml of PBS at pH 7.41; the only difference was that the sample was centrifuged. The supernatant was placed in a UV cell for the experiment. Each experiment was done in triplicate, and the Q-test was applied.

Nitric Oxide Modification of Polyamine Derivatives

After 8 days of reaction with NO, the solvent was removed from the reaction flask producing the sodium salt of the NONOate, which UV spectroscopy showed the absorption in the range of 240-260 nm. The addition of the sodium salt of the solvent increases the hydrophilicity of the species making them more hydrophilic; as a consequence they dissolve easily in aqueous solutions. This modification did not show a relevant effect on nitric oxide release of the NONOate in non-salt form. The extinction coefficient and NO release profiles are summarized in FIG. 7. The kinetics profiles of these NO donors is in the range of 0.5-2.0 hours at 37° C., which is comparable with 3-morpholinosydnonimine hydrochloride (SIN-1), which was found to be 1-2 hours in PBS pH 7.4 at 37° C. SIN-1 has been shown to be a potent vasodilator in vivo and in vitro as well as inhibiting smooth muscle cell mitogenesis and proliferation.

Loading and Stability of NONOates in an Anionic Exchange Resin

A 1×4 400 ionic exchange resin is a cationic resin, which consists of trimethyl benzyl ammonium chloride (TMBAC) ($Cl^-Me_3^+$—N~$CH_2$-Ph) is available as DOWEX. Chloride ion has a strong affinity for this resin; a high concentration of sodium hydroxide was required in order to exchange the chloride ions with hydroxyl groups. The exchange of the chloride ions was confirmed by a negative flame test; this was not observed with the treated resin. This process facilitates the attachment of the NONOates and also prevents decomposition of the NO donor.

Figure 3:
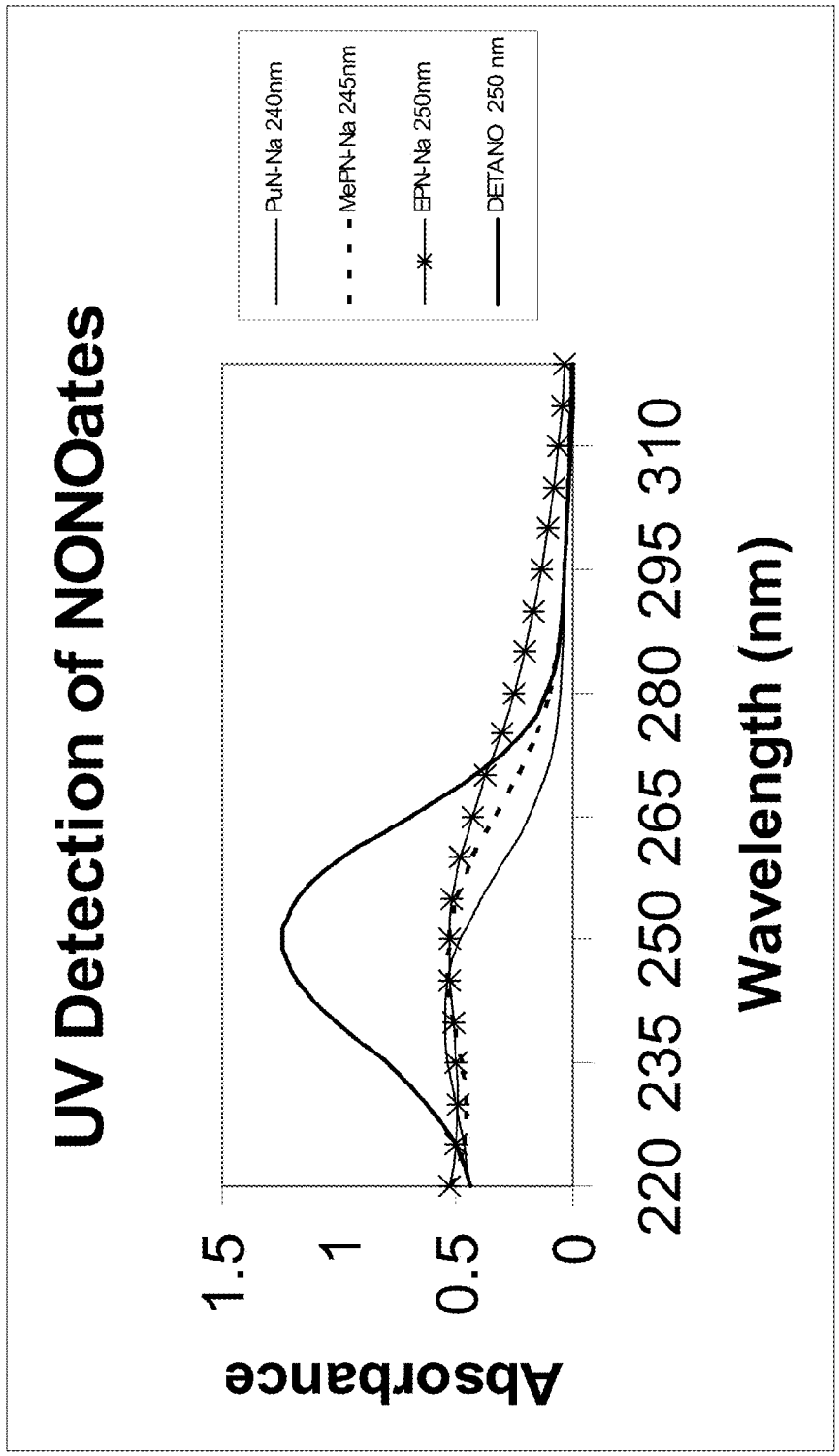
FIG. 3 is UV detection of polyamine NONOates in 0.1M of NaOH.
Figure 4:
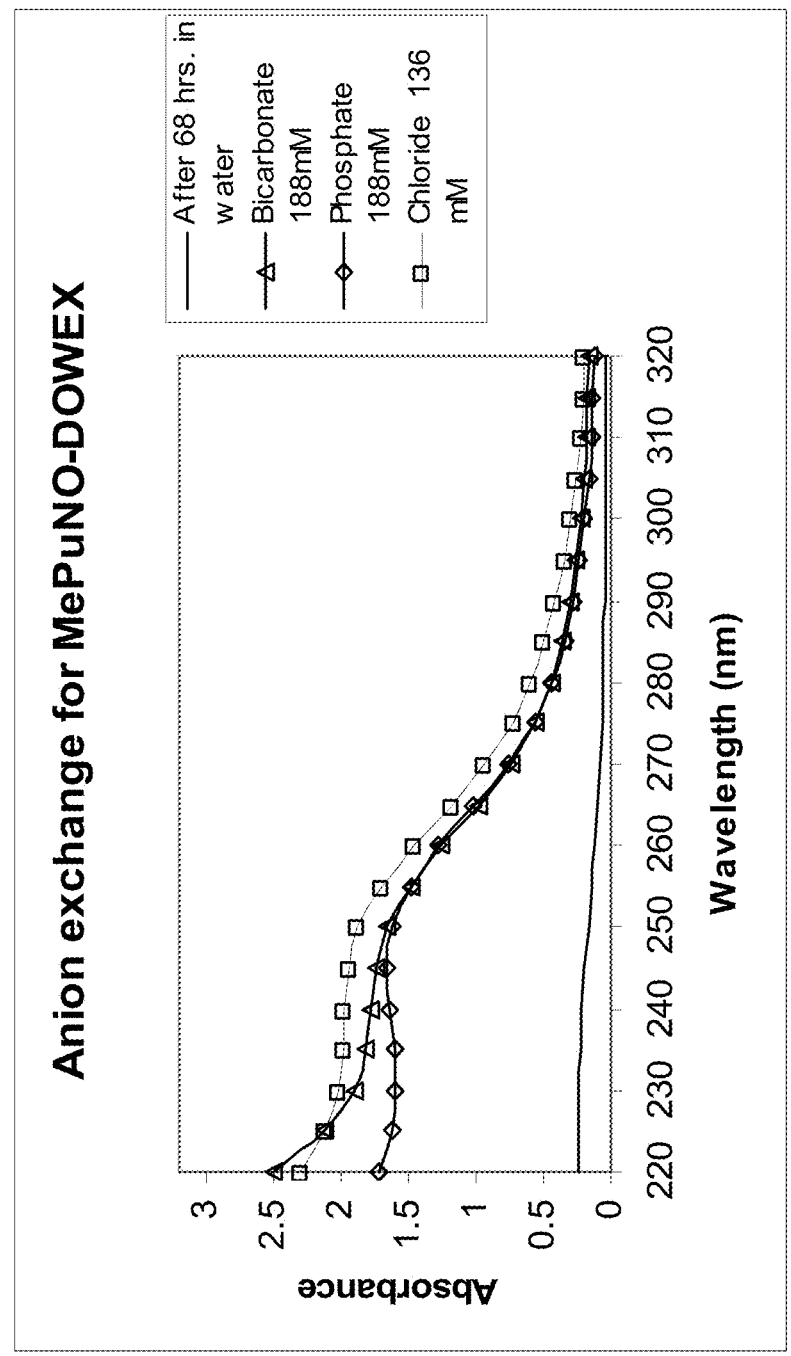
FIG. 4 after at least 68 hours in deionized water at room temperature, the subject NONOate beads showed no absorption between 245-260 nm. As shown in the plot, an anion is required to exchange the NONOate.
Figure 5:
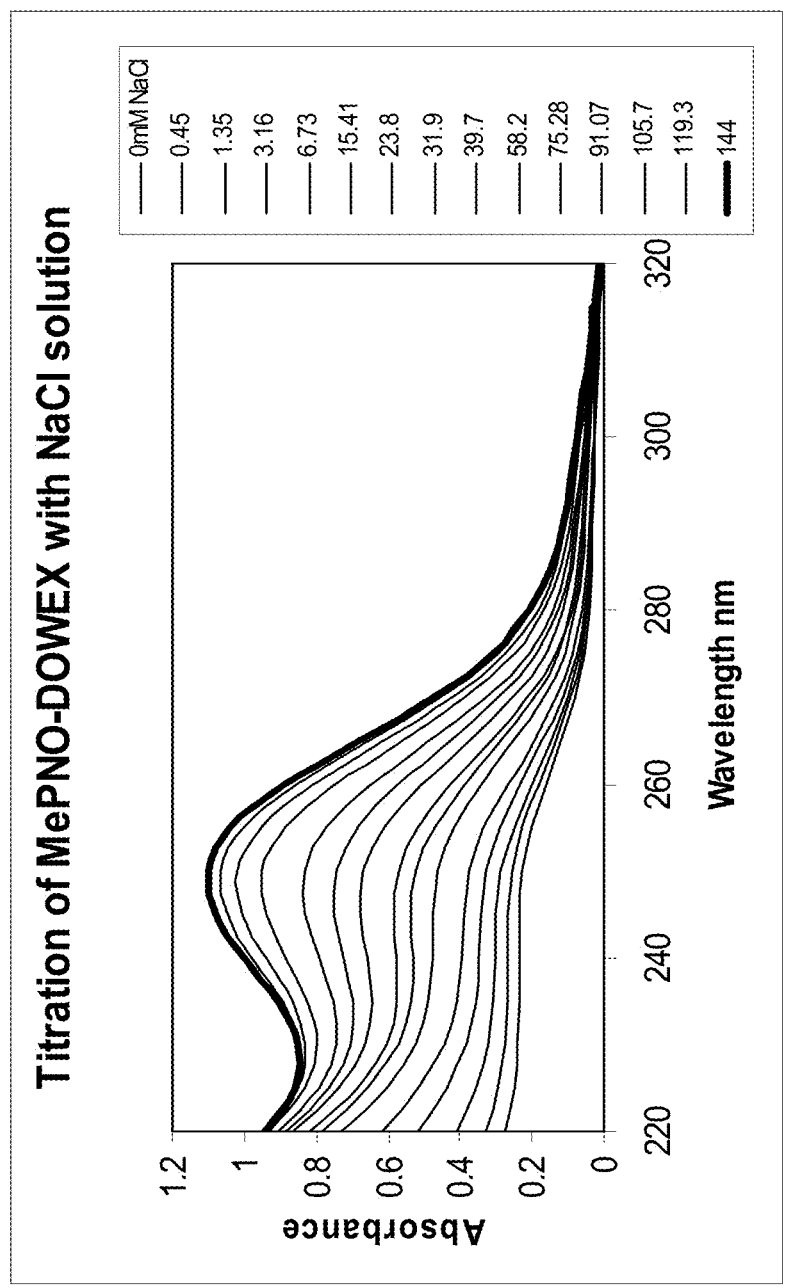
FIG. 5 is titration of 4.3 mg of MePN with an ion exchange resin (MePN-IER) with 1M solution of NaCl.
Figure 6:
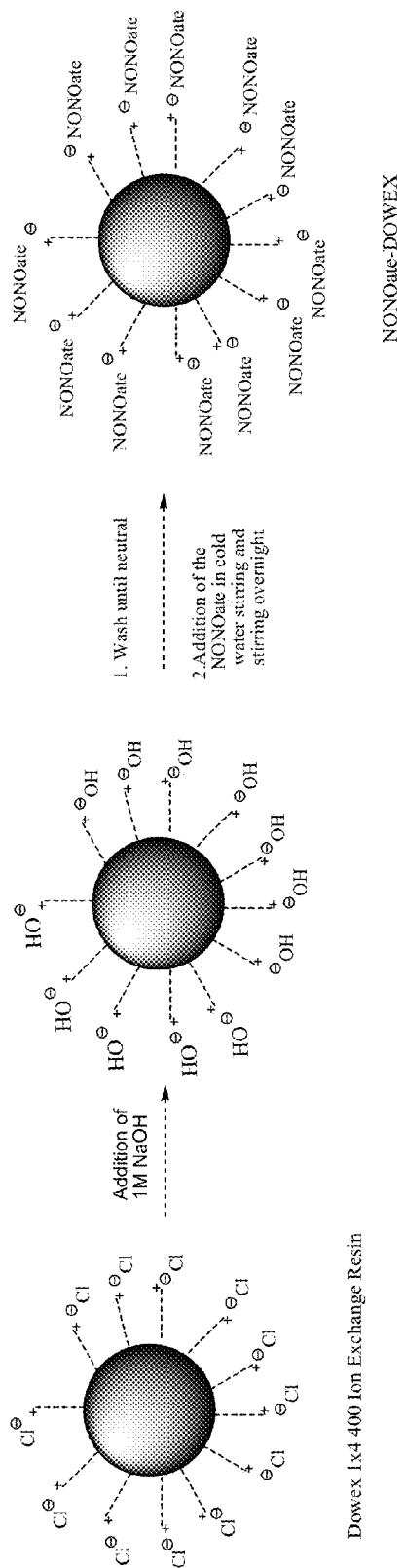
FIG. 6 is a diagram of the loading of the diazeniumdiolates with an ionic exchange resin.

The stability of the complex NONOate-IER was evaluated by leaving the sample in water at room temperature along with exposure to light. For at least 68 hours, the sample appeared to be stable under such conditions. The exchange of the NONOate was successful with the addition of an anion, in this case chloride ion. Once released, the NONOates show absorption at their maximum wavelength (see FIG. 3). However, other anions such as iodide, carbonate, bicarbonate, nitrate and phosphate were able to exchange the NONOate from the resin. The concentration of the anion required to exchange the NONOate varies from 50 mM to 144 mM (in the case of sodium chloride (see FIG. 4), which is close to the concentration of the saline solution (136 mM).

Kinetic profiles of the NONOates that were released from the resin are summarized in FIG. 8. The behavior of the NO release from the NONOates that had been attached to the resin was similar to the "free" salt form of those NONOates. There are some increases for DETAN and EPN and a decrease for MePN. The synthesized polyamines kept the same range of 0.5 to 3 hours for the NO release, which was observed on the free sodium salt diazeniumdiolates (see FIG. 7).

Various modifications and alterations that do not depart from the scope and spirit of this invention will become apparent to those skilled in the art. This invention is not to be duly limited to the illustrative embodiments set forth herein.

What is claims is:

1. A method of producing nitric oxide comprising the steps of:
   replacing anions on an anionic exchange resin with hydroxide ions to create an hydroxide-functionalize exchange resin;
   thereafter reacting a NONOate with the hydroxide-functionalized exchange resin to create a NONOate exchange resin; and
   thereafter contacting the NONOate exchange resin with a salt.

2. The method of claim 1, further comprising adding the NONOate exchange resin to a gel or a cream, wherein said step of contacting includes introducing a salt to the gel or cream.

3. The method of claim 1, wherein the NONOate is selected from the group consisting of ethyl putreanate diazeniumdiolate sodium salt, methyl putreanate diazeniumdiolate sodium salt, putreanine diazeniumdiolate sodium salt, and diethylenetriamine diazeniumdiolate.

4. The method of claim 1, wherein the step of replacing anions on an anionic exchange resin with hydroxide ions to create an hydroxide-functionalize exchange resin is performed by combining the anion exchange resin with a sodium hydroxide solution.

5. The method of claim 1, wherein the anion exchange resin includes trimethyl benzyl ammonium groups.

6. The method of claim 1, wherein the salt is sodium chloride, sodium phosphate, or sodium acetate.

7. The method of claim 1, wherein the salt contains an anion selected from the group consisting of chloride, iodide, carbonate, bicarbonate, nitrate and phosphate.

8. The method of claim 2, wherein the salt in introduced to the gel or cream from skin or tissue.

* * * * *